US012788426B2

(12) United States Patent
Umar et al.

(10) Patent No.: US 12,788,426 B2
(45) Date of Patent: Nov. 10, 2026

(54) FOLLICLE UNIT EXCISION DEVICE AND METHOD OF USE

(71) Applicant: Sanusi Umar, Manhattan Beach, CA (US)

(72) Inventors: Sanusi Umar, Manhattan Beach, CA (US); Andrew Namminga, Austin, TX (US)

(73) Assignee: Sanusi Umar, Manhattan Beach, CA (US)

( * ) Notice: Subject to any disclaimer, the term of this patent is extended or adjusted under 35 U.S.C. 154(b) by 272 days.

(21) Appl. No.: 18/704,159

(22) PCT Filed: Sep. 1, 2023

(86) PCT No.: PCT/US2023/031834
§ 371 (c)(1),
(2) Date: Apr. 24, 2024

(87) PCT Pub. No.: WO2025/048832
PCT Pub. Date: Mar. 6, 2025

(65) Prior Publication Data

US 2026/0157770 A1 Jun. 11, 2026

(51) Int. Cl.
*A61B 17/3205* (2006.01)
*A61B 17/00* (2006.01)
*A61B 17/32* (2006.01)

(52) U.S. Cl.
CPC .................. *A61B 17/32053* (2013.01); *A61B 2017/00039* (2013.01); *A61B 2017/00398* (2013.01);
(Continued)

(58) Field of Classification Search
CPC .... A61B 17/32053; A61B 2017/00039; A61B 2017/00398; A61B 2017/00752; A61B 2017/320064
See application file for complete search history.

(56) References Cited

U.S. PATENT DOCUMENTS

2010/0125287 A1* 5/2010 Cole ................ A61B 17/32053 606/133
2014/0031839 A1 1/2014 Umar et al.
(Continued)

FOREIGN PATENT DOCUMENTS

CN 101702083 5/2010
EP 3031414 A1 6/2016

OTHER PUBLICATIONS

Extended Search Report dated Jan. 16, 2025, issued in corresponding European Application No. 23880916.
(Continued)

*Primary Examiner* — Sarah A Long
(74) *Attorney, Agent, or Firm* — Millen, White, Zelano & Branigan, P.C.; Christopher W. Brody

(57) ABSTRACT

A follicle unit excision device controls an operating speed for the punch of the device for cutting and obtaining a graft based on skin contact with a cutting tip of the punch. The device uses one or more parameters associated with the rotation of the punch, for example, rotational speed or motor voltage, that is affected when the punch contacts skin of a patient. The skin contact and one or more thresholds associated with the parameter are used to trigger the motor to rotate at an operating speed so that the device can be used for follicle unit excision.

11 Claims, 2 Drawing Sheets

(52) U.S. Cl.
CPC ............... *A61B 2017/00752* (2013.01); *A61B 2017/320064* (2013.01)

(56) References Cited

U.S. PATENT DOCUMENTS

| | | | | |
|---|---|---|---|---|
| 2015/0018844 A1* | 1/2015 | Harris .............. | A61B 17/32053 606/133 |
| 2016/0166272 A1* | 6/2016 | Shiao ............... | A61B 17/32053 606/133 |

OTHER PUBLICATIONS

Trivellini Roberto et al. "The Trivellini system and Technique", International Society of Hair Restoration Surgery, vol. 28, No. 5, Sep. 1, 2018, pp. 188-190.

* cited by examiner

FOLLICLE UNIT EXCISION DEVICE AND METHOD OF USE

FIELD OF THE INVENTION

A follicle unit excision device includes a motor control that allows the punch of the device to rotate at an idle speed when not being used for follicle unit excision and then then shift to an operating speed based on the cutting tip of the punch contacting skin and subsequent changes in parameters associated with the device as a result of skin contact.

BACKGROUND OF THE INVENTION

Follicular Unit Extraction ("Fue") is a surgical hair transplantation technique that involves moving skin containing hair follicles from one part of the body (the donor site) to bald or balding parts (the recipient site). Hair naturally grows in follicles that contain groupings of 1 to 4 hairs, and the transplant technique typically moves the 1-4 hair "follicular units" from the donor site to the recipient site.

The follicle units (sometimes referred to as "grafts") are typically removed from the donor site using punches of between 0.7 mm and 1.25 mm in diameter. The punches are typically tubular bodies having a skin-contacting cutting edge. The tubular bodies are typically mounted in a hand-held electric-powered tool that causes the punch to rotate or oscillate as the cutting device is brought into contact with the donor site. Sometimes, the tubular bodies are used manually.

Hair follicles are very easily broken during the removal, and broken follicles are unlikely to be successfully transplanted. One of the major causes of low yield in Fue is attributable to desiccation forces imparted on the graft following its dissection from its tissue investiture; more specifically, as it is pulled from the donor site, and as it is placed in a physiological holding solution such as normal saline, ringer's lactate, etc., for subsequent transplantation at the recipient site.

One known Fue device uses a suction mechanism to suck out the graft immediately following desiccation and propel it pneumatically through a tube into a collection canister that contains a physiological medium. The sucked graft is subjected to traumatic forces as it is funneled at high force and velocity out of the donor site and through the narrow tube, banging against the tube wall as it is propelled to the canister. Additionally, sucking and pulling the graft as it is cut from the donor site creates a risk of transection from the combined vectors of pulling and rotating as the rotating cutting device creates a like rotation in the graft being extracted while it is tethered to the surrounding tissue at the donor site. Moreover, the suction effect strips the graft of some of its protective tissue investiture, further diminishing its protection from damaging desiccating factors as well as trauma.

Another known Fue device is disclosed in U.S. Pat. No. 9,095,368 to Umar and this patent is incorporated in its entirety herein. This Fue device is directed to the elimination of, or at least a substantial reduction in, the desiccation forces to which extracted follicle units are subjected during the extraction process to thereby increase the yield of successfully transplantable follicles harvested from the donor site. This Fue device comprises a handpiece configured to securely hold a follicle punch, and utilizes fluid irrigation and a pumping mechanism whereby fluid is delivered to the cutting edge of the punch during the cutting and extraction of the follicle unit. In its preferred embodiment, the fluid is delivered through the punch's lumen. As an additional feature, the fluid is selectively delivered in greater quantity through the punch lumen to clear impacted follicles and/or debris from the punch. The fluid can be carried to the cutting edge in any of a number of ways. For example, it can be delivered through the lumen of the punch and directed outwardly towards the cutting edge at the skin-contacting end of the punch or delivered to the punch via a conducting path external to the punch.

Any number of different kinds of fluids can be used, including physiologic or other solutions. These fluids may also be a fluid that may or may not have been proven to prolong or sustain graft or tissue viability. In addition, the handpiece is preferably configured to cause punch rotation during at least the cutting phase of the extraction process.

Currently, all follicular unit excision (Fue) methods of hair harvesting for transplantation require the use of a punch mounted on a drill machine, the punch used to cut a circular path around each hair follicle or follicles to separate it from the surrounding tissue holding it to the scalp. After the circular cutting or scoring step is completed, the hair follicle (s), which are now called the graft, is pulled out.

The Fue devices require that the punch, which is mounted on a handpiece, begins to rotate for cutting purposes when either a button is pressed by the hand or finger of the device user or a foot pedal or the like is pressed by the foot of the user.

One device, characterized as the Trivellini system, has a more user-friendly and efficient system regarding rotating the punch, wherein the user bypasses the button press methods to start rotation of the punch. In the Trivellini system, the punch rotates once it touches the skin. This is accomplished by the incorporation of a suction vacuum that continuously sucks air through the mouth/opening at the distal end the punch. With a vacuum being pulled through the punch, a closing of the opening at the distal end of the punch, i.e., applying the punch to contact skin, the vacuum pressure increases. This vacuum pressure increase is sensed and a punch rotating mechanism is activated and the punch begins its rotation in order to obtain the graft.

Since some Fue devices employ a vacuum, adapting such devices using a vacuum to initiate rotation of the punch is easily done. However, not all Fue devices use a vacuum, see for example, the device of the Umar patent noted above that uses fluid as a part of obtaining the graft. Thus, it would be complicated to modify this kind of devices and others that may not use a vacuum system to obtain a graft.

It is also known to initiate movement of a tool such as a knife by using an electrical grounding circuit, wherein contact with the knife completes the circuit so that the knife could start to move. The problem with these kinds of devices is that some patients may have electric devices such as pacemakers or automatic heart defibrillators on or in the patient's body. Thus, using an electrical grounding circuit can potentially interfere with the devices of these patients and any such system not a desirable option when using a Fue device on such patients.

As such, there is a need for improvements in Fue devices that require some additional manipulation by the device user to initiate the rotation of the punch of the device or require the use of a vacuum. The present invention responds to this need by providing an improved Fue device and method of use, wherein the Fue device does not need a separate control to rotate the device punch at its operating speed for graft removal or a vacuum source.

SUMMARY OF THE INVENTION

The invention provides improvements in Fue devices used to obtain follicle units for transplantation purpose. One aspect of the invention is the actual device that performs the cutting necessary to obtain a graft for transplantation. This follicle unit excision device includes a housing to be held in the hand of a user, i.e., a handpiece. The handpiece includes a punch, with a portion extending from the handpiece, the punch including a cutting tip at a distal end of the punch. The handpiece also includes a motor that cooperates with the punch for rotation thereof.

The handpiece also includes means for obtaining a graft using the punch and cutting tip, with these means being any known type that are typically used in Fue devices.

The handpiece also includes a means for rotating the punch at an idle speed state when the punch is not in contact with skin of a patient and then rotating the punch at an operating speed state based on contact of the cutting tip of the punch with the skin of a patient supplying the graft.

As part of the means for rotating the punch at the idle speed state and then rotating the punch at the operating speed state, a controller can be provided that is configured to rotate the punch between the idle speed state and the operating speed state, the idle speed state rotating the punch at a first rotational speed, the operating speed state rotating the punch at a second rotational speed greater than the first rotational speed. The second rotational speed is designed for cutting skin and obtaining a graft, the operating speed state being triggered by the cutting tip contacting skin of a patient and a change in parameters associated with the handpiece indicating the skin contact and triggering the motor to go into the operating speed state. Examples of such parameters include one or both of, a decrease in the first rotational speed of the idle speed state below a predetermined threshold speed, and an increase in a voltage of the motor at the idle speed state that is above a predetermined threshold voltage. The control includes the one or more threshold values that set limits for triggering of the motor to go into the operating speed state.

In a more preferred mode, both the decrease in rotational speed in the punch and increase in voltage of the motor are used to establish the operating speed state.

The device can also include a feature or means wherein the second rotational speed can be determined by the user of the device by selecting from a plurality of predetermined second rotational speeds or by having the ability to vary the second rotational speed once the Fue device is in the operating speed state.

Another option for the device is the ability to include a time lapse to occur before the operating speed state commences. This time lapse could be a default condition for the device or be variable and controlled by the user.

While the idle state speed and operating state speed can vary, a typical range for the idle speed state speed could be between 0.5 RPM and 3 RPM, with a more preferred range of 0.5 RPM to 1 RPM. Similarly, the operating state speed could be between 12,000 RPM and 15,000 RPM, with a more preferred range of 12,000 RPM to 14,000 RPM. The time lapse can also range between 0.2 milliseconds (ms) and 2 ms, and preferably between 0.2 ms and 0.5 ms.

Another aspect of the invention entails the method of cutting skin and obtaining a graft from a patient using a follicle unit excision device. The inventive method is improved over prior art methods as the follicle unit excision device described above is used for cutting skin and obtaining the graft. After the graft is obtained, the punch reverts to the idle speed state as it is no longer in contact with skin and stays in the idle speed state until another procedure is initiated by skin contact for cutting and obtaining a graft.

DETAILED DESCRIPTION OF THE INVENTION

The inventive Fue device offers significant improvements over other types of devices currently used in the hair transplantation field. With the inventive device, the need for a vacuum arrangement as part of the handpiece to trigger rotation or oscillation of the punch is avoided. Likewise, systems that would require some kind of electrical grounding for triggering the rotation of the punch can be avoided. Since the control of the rotation of the punch is independent of the means used by the handpiece to recover the graft from the patient, the control system employed for punch rotation can be used in any type of Fue device.

Figure 1:
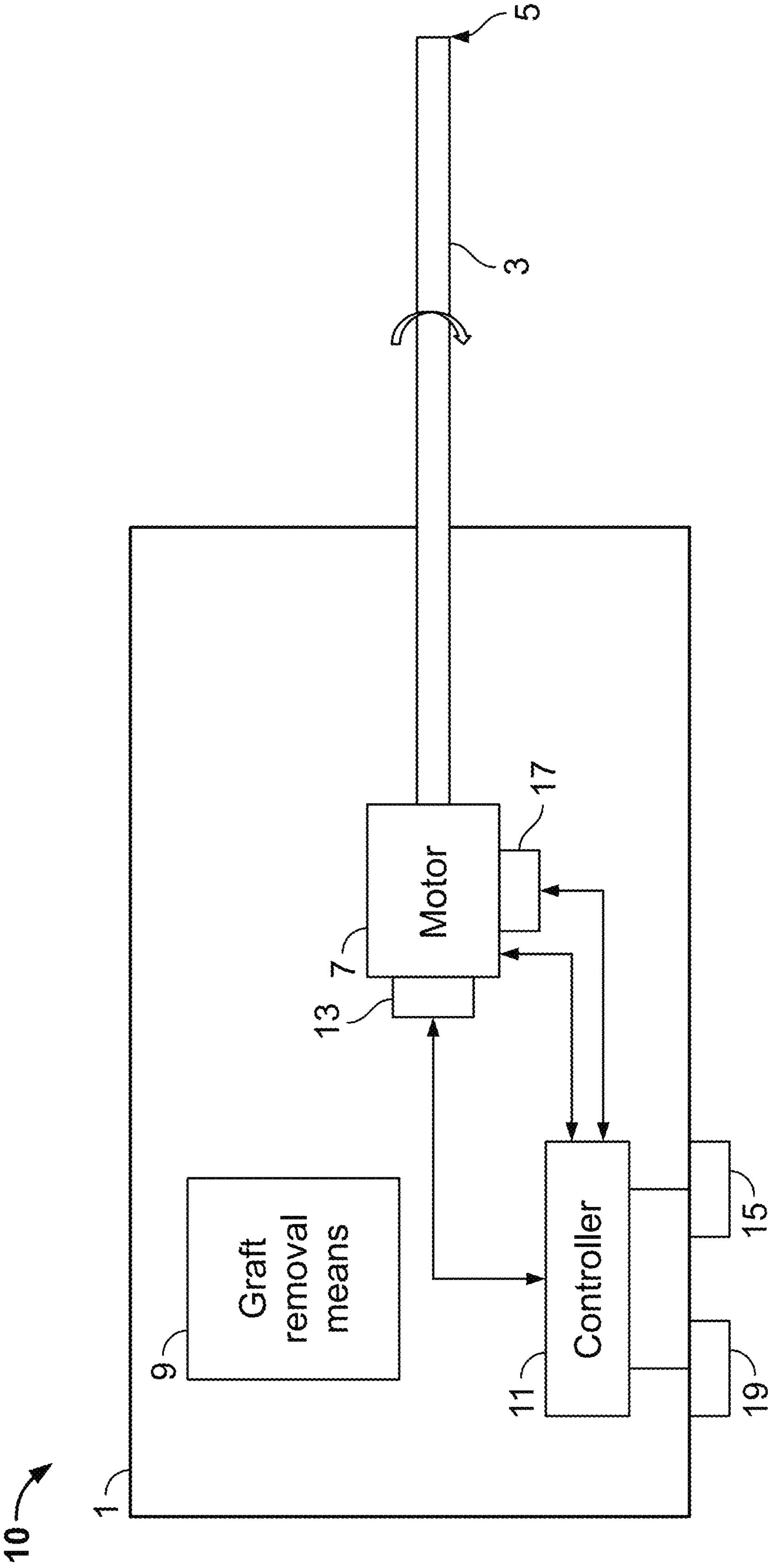
FIG. 1 shows a schematic representation of a first embodiment of the inventive Fue device.

FIG. 1 shows a schematic representation of a Fue device that is designated by the reference numeral 10. Since many of the features of these kinds of Fue devices are well known, the features are represented in a schematic manner as opposed to the detailed manner that is found in the Umar patent noted above.

As is well known in the art, these kinds of devices include a handpiece 1 and a punch 3 having a cutting tip 5. Since the handpiece is shown in a schematic way, the features allowing it to be handheld are not illustrated. Such features can be gleaned from the handpiece disclosed in the Umar patent noted above.

The handpiece can be battery powered or powered through AC or DV voltage. Since the power connection to the handpiece and its components is also well known, the details of these connections are not necessary for understanding of the invention.

The handpiece 1 includes a motor 7 that is designed to rotate the punch 3 for cutting to obtain a graft. The details of how the motor rotates the punch are also well known so that only a schematic representation of the motor and punch is needed for understanding of the invention. The term rotation as used herein also includes an oscillating movement of the punch.

The device 10 also includes a graft removal means 9, which is shown schematically as well as the graft removal means associated with the device can be any known type that is available in the prior art. As mentioned above, the graft removal means 9 could be a vacuum system, wherein the graft, once cut out using the cutting tip is sucked into the punch and deposited into a container. Another kind of graft removal means could be the fluid assisted type as disclosed in the Umar patent. Since these kinds of systems as part of a Fue device are well known, a detailed explanation of them is not required for understanding of the invention.

Referring again to the motor 7, and as noted above in the discussion of the prior art devices, the operation of the motor in the prior art devices would be controlled by a button on the handpiece 1, or a foot pedal connected to the housing, or a vacuum system that would operate the motor once the cutting tip 5 contacted skin to block the opening at the cutting tip and increase vacuum pressure, thereby providing a signal that the motor should begin rotation for obtaining a graft.

In the inventive device 10, a controller 11 is provided with a number of functionalities as part of the device operation. In one functionality and once power is supplied to the handpiece by activating an on/off switch (not shown), the controller is configured to operate the motor 7 in an idle speed state or punch slow rotation state, e.g., a revolution per minute (rpm) rate of 0.5-10. Other rotation speeds could be used to rotate the punch in the idle state.

The second functionality relates to increasing the speed of rotation of the punch so that the handpiece is in an operating state for obtaining grafts without the need for some kind of action of the operator by the operation other than to bring the punch of the Fue device in contact with a patient's skin. This second functionality occurs as a result of having the controller including means configured to measure a parameter associated with the Fue device and assess a change in the parament that occurs as a result of contact of the slow rotating cutting tip of the punch with skin.

One parameter of the Fue device that can be monitored and used to determine when to trigger the motor to be at an operating speed is monitoring the speed of rotation of the slow rolling punch in the idle speed state. When the punch comes into contact with skin, the friction will cause a decrease in the rotational speed of the punch. The controller would include a speed sensor 13 that would sense the rotational speed of the motor and punch. The controller also knows the idle speed state speed and a predetermined speed threshold that is used as part of triggering the motor to go to the operating speed state. A decrease in speed from the idle speed state speed would then be an indication that the punch is in contact with the skin. The rotating speed of the punch is then compared to the predetermined speed threshold. If the speed is below the speed threshold, this is an indication that the motor should be triggered to be in the operating speed state.

The operating speed could be a preset value. In the alternative, the controller could have an input 15 on the handpiece that would allow the user to select a different operating speed depending on the conditions of the cutting and graft obtaining. This input could take any form, analog or digital, to allow the handpiece user to select a rotational speed of the punch for the cutting and graft obtaining procedure. The input 15 could permit selection of an operating speed from a number of preset operating speeds. In an alternative, the input could be variable speed control, wherein once the handpiece is in the operating speed state, a user to could determine the operating speed based on user preference and manipulation of the input 15 rather using than a preset speed.

Another parameter that can be measured as part of the contact between the slow rolling punch and skin is voltage at the motor. When the cutting tip contacts the skin, a load is placed on the motor and an increase in voltage occurs as compared to the voltage of the motor when in the idle speed state (idle speed state voltage). The cutting tip sees a resistance to rotation as a result of the friction of the touch with the skin and this resistance translates to an increase in voltage that is sensed by voltage meter 17. A predetermined voltage threshold is also established as part of the voltage monitoring aspect. When the voltage increase surpasses the predetermined voltage threshold, thus confirming that the cutting tip 5 is sufficiently in contact with skin for cutting and graft obtaining purposes, the controller can then trigger the motor to increase the speed of rotation of the punch to the operating speed, i.e., revolutions per minute (RPM) being an example thereof. The set limit of threshold would be a sufficient voltage increase that would confirm that the punch is sufficiently in contact with the skin to trigger the motor to rotate at the operating speed.

It should be understood that either the voltage sensing mode or the speed sensing mode could be used to trigger the motor to rotate the punch in the operating speed state. The two parameters could also be combined so that when the sensed speed of the motor is less than the speed threshold and the sensed voltage of the motor is greater than the voltage threshold, the controller knows that the motor should then rotate the punch at the operating speed for cutting and graft obtaining.

While punch rotation and motor voltage are examples of two parameters useful for monitoring conditions when the cutting tip of the punch comes into contact with the skin of a patient, another parameter could be used, e.g., current, that is measured in connection with the motor as an indicator that the cutting tip is in contact with skin and the motor should be triggered to rotate at the operating speed for a given procedure.

The selection of the idle speed, the speed threshold, and voltage threshold can be left to the device manufacturer. In the alternative, the controller could be set up so that the user could change the idle speed, and the threshold values for speed and/or voltage if the circumstances of a particular procedure would dictate that such a change in a default idle speed and default thresholds is needed.

The device 10 could also employ a time lapse feature. That is, a time lapse could be added between the time the voltage is increased to go above the voltage threshold limit and/or the speed is reduced to be less than the speed threshold limit rotational speed and the start of the rotation of the cutting punch to the operating speed, e.g., 500-1000 ms, etc. The time lapse could be a default condition for the device, with a fixed time lapse that would not be adjustable by the user of the device 10. In an alternative embodiment, the handpiece could include another input 19 that represents an ability of the user to select a particular time lapse to occur between the time when the threshold requirements of the controller are satisfied and the device is to go to the operating speed state depending on the needs of the user.

As noted above, the Fue device could also include the capability of selecting an operating speed for a given procedure either by selecting a speed from a menu of predetermined speeds or having a variable speed control that would allow the use to set the operating speed as conditions dictate for a given procedure. This capability is represented by reference numeral 19 on the handpiece 1 of FIG. 1. A typical operating speed of rotation range of a punch in an Fue device is 12,000 to 15,000 RPM. The operator of the Fue device determines what speed is desirable for a given procedure so that the actual speed of rotation of the punch could vary within this range.

Figure 2:
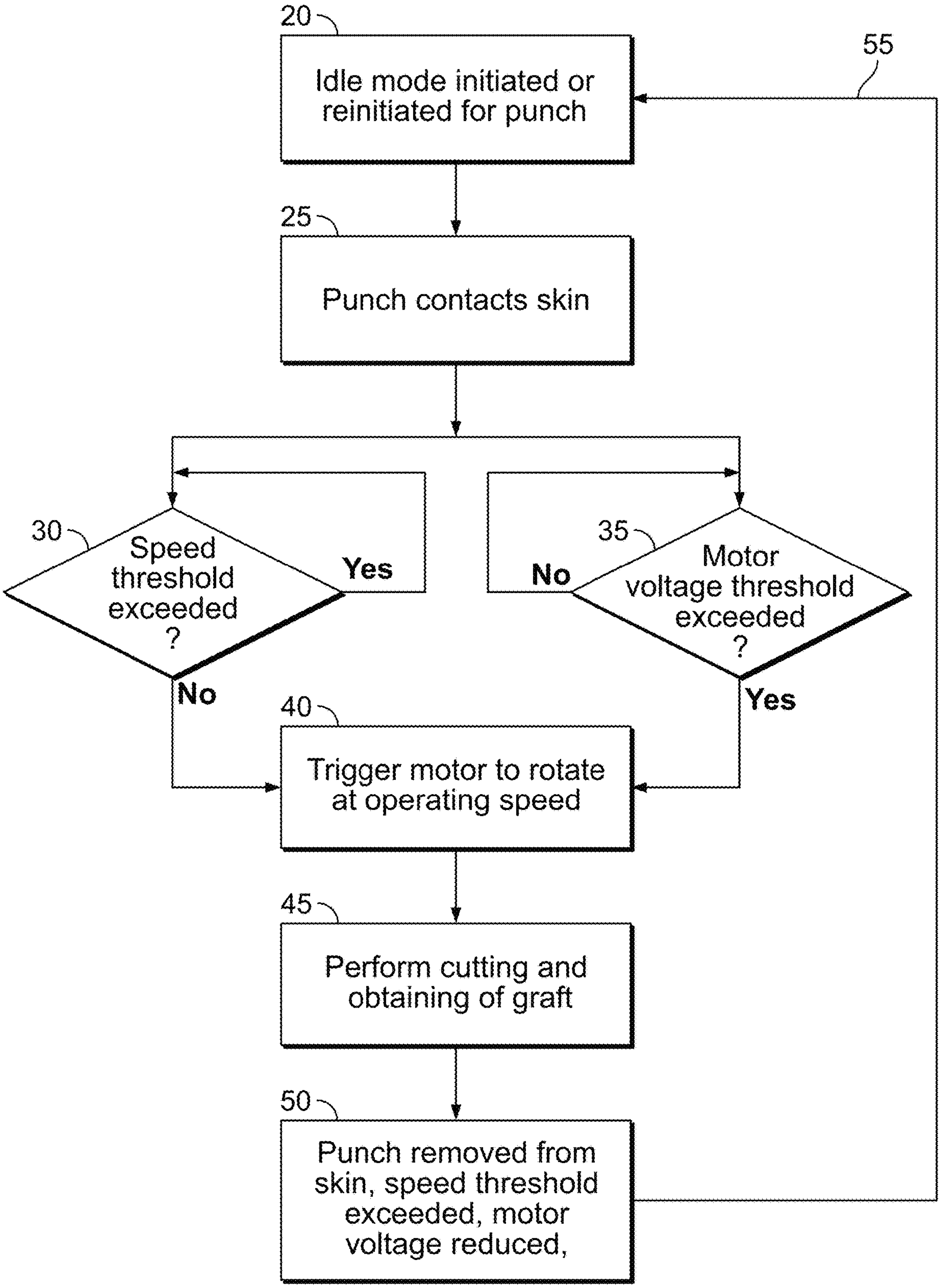
FIG. 2 shows an exemplary flow chart showing one mode of operation of the inventive Fue device.

FIG. 2 shows a flow chart that outlines an example of an operation of the device in the idle speed state and operating speed state. In this example, both the change in speed of the rotation of the punch and the change in voltage of the motor are monitored and used to trigger the motor to increase the speed of rotation of the punch to the operating speed. However and as noted above, just the speed change or the voltage change could be used individually to trigger an increase of the rotation of the punch to the operating speed.

A first step as a "Start" is designated by the reference numeral 20 and signifies powering of the device 10 on for use. The device normally defaults to the idle speed state when powered on. In the idle state, the motor 7 slowly rotates the punch 3 to the RPM set by the controller 11. A time lapse may occur between the powering of the device and the slow roll of the punch.

In a second step 25, with the motor 7 slowly rotating the punch 3, e.g., between 0.5 and 3 RPM, the handpiece operator touches the skin of the patient with the cutting tip 5. This contact between the cutting tip of the punch and the skin results in two things happening. One is an increase in the measured voltage for the motor above the voltage measured in the idle state. The other is a decrease in the rotational speed of the punch from that of the idle state. In the control scheme illustrated in FIG. 2, both the reduction in rotation speed of the punch and the increase in voltage for the motor are used to trigger the motor to rotate the punch at the operating speed for cutting and obtaining of a graft.

The effect of speed reduction is addressed in step 30. Here, the controller 11 has a predetermined threshold speed of rotation of the punch that indicates that the punch and cutting tip are primed for a cutting operation. For example, if the idle speed state rotation is 5 RPM, the threshold speed would be set to be lower than the idle speed state rotation, e.g., 2 RPM. If the speed threshold is exceeded, e.g., the rotation of the punch is 4 RPM, the controller 11 takes no action. If the speed of rotation of the punch is less than the threshold value, e.g., 1 RPM, the controller than sends a signal indicating that the punch should be rotated at the operating speed. The speed threshold could also be the idle speed, such that when the cutting tip contacts skin and the rotation of the punch falls below the idle speed, the triggering of the motor to the operating speed state can be initiated.

A similar control scheme is associated in step 35 for the monitoring of the voltage of the motor. For example, for an idle speed state rotation, the motor voltage would have a certain value, e.g., 0.5 volts. The threshold voltage would be set to be higher than the voltage associated with the idle state, e.g., 20% greater than the motor voltage at the idle speed state. Using the 0.5 volts as an example of voltage measured in the idle state, the voltage threshold would be 0.55 volts. If the voltage threshold is not exceeded, e.g., the voltage of the motor is sensed as less that the 20% greater value, i.e., less than 0.55 volts, the controller 11 takes no action. If the measured voltage of the motor exceeds the threshold value of 0.55 volts, the controller than sends a signal indicating that the punch should be rotated at the operating speed. The voltage threshold could be a value slightly greater than the idle state voltage or it could be a value much greater than the idle state voltage if so desired, e.g., an exemplary idle state voltage would be 0.5 volts and a threshold voltage would be 20% greater than that or 0.55 volts. It should be understood that the 0.5 volt measurement for the idle speed is only an example of a typical voltage measured for a given idle speed. Since the idle speed range can vary from 0.5 RPM to 10 RPM, the typical voltage measurement can also vary accordingly as the voltage is linked to the RPM of the punch.

When using both speed and voltage to trigger the motor to run at the operating speed, a combiner step 40 is included. In this step, if both the sensed speed of the punch is less than the speed threshold and the sensed voltage of the motor is greater than the voltage threshold, the controller then triggers the motor to run at the operating speed for cutting and graft obtaining, the cutting operation corresponding to step 45. In the mode wherein only a single parameter associated with the handpiece 1 is affected by skin contact, e.g., either the decrease in the rotational speed of the punch from the idle speed state or the increase in the voltage of the motor from the idle speed state, is used to initiate the operating speed state, getting a no signal in step 30 or a yes signal in step 35 would trigger the motor to the operating speed state and there is no need for a combiner to ensure that both steps 30 and 45 are completed to initiate the operating speed step.

Once a cutting operation is completed and the cutting tip is removed from skin, the rotational speed of the punch will increase beyond the speed threshold and the measured voltage of the motor will decrease below the voltage threshold. In this condition, the controller would have the handpiece revert to the idle speed state until another cycle of cutting and graft obtaining is started. This reversion to the idle state is represented by step 50 and arrow 55 indicating a return to the idle speed state. In other words, a work cycle wherein the motor is triggered to run at the operating speed and then revert to the idle speed state when the cutting tip is no longer in contact with the skin is completed and the Fue device is ready for initiation of another work cycle via skin contact meeting the threshold or thresholds to initiate the operating speed state of the punch and again terminate it once the cutting operation is over and the cutting tip of the punch is removed from the skin.

The specifics relating to the controller, the speed control 15, the time lapse control 19, the use of a speed sensor 13 and voltage sensor 17 in connection with the motor 9, are not necessary for understanding of the invention. In addition, providing the necessary means to monitor the speed of the motor in light of a speed threshold, to monitor the voltage of the motor in light of a voltage threshold for setting the operating state of the Fue device, to provide a time lapse capability and speed variation option for the operating speed would be within the skill of the art and illustrating the necessary electrical connections, etc. are not essential for understanding of the invention.

While any motor that would be functional in an Fue device can be used as part of the inventive device, an example of such a motor is a Precision DC stepper motor. Likewise, an example of the speed sensor that would allow determination of rotation speed decrease from the idle speed state would be an encoder capable of monitoring physical RPM. An example of a voltage sensor that would allow determination of a voltage increase from the idle speed state would be a means to measure the current draw on the system and display the increase in terms of volts. These components are only examples and other kinds of motors and sensors having the capability to monitor the change in rotational speed of the punch and voltage/current of the motor can be used as part of the inventive Fue device and its method of use. For example, an encoder-type device could be employed for monitoring the change in voltage associated with the punch rotation slow down due to skin contact.

The invention also includes a method of using the Fue device when seeking to obtain grafts from a patient for transplanting. This method is an improvement in the known methods that use prior art devices that require some type of an on-off switch to get the device into an operating state to perform a procedure or require the use of vacuum to reach the operating state. Using the inventive device, a user can manipulate the device from its slow rolling idle speed state to where the cutting tip of the punch contacts the skin of a patient, wherein changes in parameters associated with the handpiece with respect to threshold or thresholds for the device occur, e.g., rotational speed of the punch, voltage, and/or current change and these changes are used to trigger the motor of the device such that the punch rotates at the operating speed so that a skin cutting and graft obtaining procedure can be performed.

As such, an invention has been disclosed in terms of preferred embodiments thereof which fulfills each and every one of the objects of the present invention as set forth above and provides a new and improved Fue device and method of use.

Of course, various changes, modifications, and alterations from the teachings of the present invention may be contemplated by those skilled in the art without departing from the intended spirit and scope thereof. It is intended that the present invention only be limited by the terms of the appended claims.

We claim:

1. A follicle unit excision device comprising:

a handpiece, the handpiece including:

a punch, with a portion extending from the handpiece and including a cutting tip at a distal end of the punch, a motor cooperating with the punch for rotation thereof, a means for obtaining a graft using the punch and cutting tip, and a means for rotating the punch at an idle speed state when the punch is not in contact with skin of a patient and then rotating the punch at an operating speed state based on contact of the cutting tip of the punch with the skin of the patient supplying the graft.

2. The device of claim 1, wherein the means for rotating further comprises a controller configured to rotate the punch between the idle speed state and the operating speed state, the idle speed state rotating the punch at a first rotational speed, the operating speed state rotating the punch rotate at a second rotational speed greater than the first rotational speed, the second rotational speed designed for cutting skin and obtaining the graft, the operating speed state being triggered by the cutting tip contacting skin of the patient, which results in one or both of, a decrease in the first rotational speed of the idle speed state below a speed threshold speed, and an increase in a voltage of the motor as compared to the idle speed state and above a voltage threshold.

3. The device of claim 2, wherein both the decrease in first rotational speed and increase in the voltage of the motor as compared to the idle speed state are used to establish the operating speed state.

4. The device of claim 1, further including a means for selecting a second rotational speed from a plurality of predetermined second rotational speeds and/or means for varying the second rotational speed for cutting and obtaining the graft.

5. The device of claim 1, further including a means for providing a time lapse before for the operating speed state commences.

6. The device of claim 1, wherein the idle speed state ranges from 0.5 to 10.0 rotations per minute for the punch.

7. The device of claim 1, wherein the operating speed state ranges from 12,000 to 15,000 rotations per minute for the punch.

8. The device of claim 5, wherein a time for the time lapse ranges from 2 ms to 2 ms.

9. A method of cutting skin and obtaining a graft from a patient using a follicle unit excision device, the method comprising providing the follicle unit excision device of claim 1 for cutting skin and obtaining the graft.

10. The method of claim 9, wherein after the graft is obtained, the punch reverts to the idle speed state until another procedure begins for cutting and obtaining another graft.

11. The device of claim 1, wherein the idle speed state ranges from 0.5 to 3 rotations per minute.

* * * * *